US012016947B2

(12) United States Patent
Portugal Cohen et al.

(10) Patent No.: US 12,016,947 B2
(45) Date of Patent: Jun. 25, 2024

(54) COMPOSITIONS COMPRISING DEAD SEA WATER AND POLYSACCHARIDES AND USES THEREOF AS SKIN PROTECTANTS

(71) Applicant: AHAVA—DEAD SEA LABORATORIES LTD., Airport (IL)

(72) Inventors: Meital Portugal Cohen, Jerusalem (IL); Miriam Oron, Jerusalem (IL); Dror Cohen, D.N the Dead Sea (IL); Zeevi Maor, Dead Sea (IL)

(73) Assignee: AHAVA-DEAD SEA LABORATORIES LTD., Airport (IL)

( * ) Notice: Subject to any disclaimer, the term of this patent is extended or adjusted under 35 U.S.C. 154(b) by 84 days.

(21) Appl. No.: 17/399,709

(22) Filed: Aug. 11, 2021

(65) Prior Publication Data

US 2022/0008324 A1   Jan. 13, 2022

Related U.S. Application Data

(62) Division of application No. 16/324,346, filed as application No. PCT/IL2017/050861 on Aug. 3, 2017, now abandoned.

(30) Foreign Application Priority Data

Aug. 8, 2016   (IL) .......................................... 247192

(51) Int. Cl.
| A61K 8/96 | (2006.01) |
| A61K 8/73 | (2006.01) |
| A61K 31/715 | (2006.01) |
| A61K 35/08 | (2015.01) |
| A61P 17/00 | (2006.01) |
| A61P 29/00 | (2006.01) |
| A61P 39/00 | (2006.01) |
| A61Q 17/00 | (2006.01) |

(52) U.S. Cl.
CPC ................ *A61K 8/965* (2013.01); *A61K 8/73* (2013.01); *A61K 31/715* (2013.01); *A61K 35/08* (2013.01); *A61P 17/00* (2018.01); *A61P 29/00* (2018.01); *A61P 39/00* (2018.01); *A61Q 17/00* (2013.01)

(58) Field of Classification Search
None
See application file for complete search history.

(56) References Cited

U.S. PATENT DOCUMENTS

| 4,638,059 A | 1/1987 | Sutherland |
| 6,248,340 B1 | 6/2001 | Maor et al. |
| 6,582,709 B1 | 6/2003 | Maor et al. |
| 2009/0017129 A1 | 1/2009 | Ma'Or et al. |
| 2009/0047226 A1 | 2/2009 | Teckenbrock |
| 2012/0101060 A1 | 4/2012 | Thoerner et al. |
| 2014/0212513 A1 | 7/2014 | Afriat-Staloff et al. |

FOREIGN PATENT DOCUMENTS

| CN | 101011325 A | 8/2007 | |
| CN | 105616282 A | 6/2016 | |
| FR | 2795083 A1 | 12/2000 | |
| FR | 2 837 097 A1 | 9/2003 | |
| FR | 2 837 388 A1 | 9/2003 | |
| FR | 2 856 925 A1 | 1/2005 | |
| FR | 2936150 A1 * | 3/2010 | ........... A61K 31/715 |
| FR | 2 958 845 A1 | 10/2011 | |
| WO | 2015/188335 A1 | 12/2015 | |

OTHER PUBLICATIONS

Wineman et al. Journal of Cosmetic Dermatology 2012 11:183-192 (Year: 2012).*
Glycofilm® and Pollustop®: http://www.aston-chemicals.com/news/2015/10/18/pollustop/. Aston Chemicals, Pollustop for Anti-Pollution (strong in vivo, ex vivo and in vitro data), Aug. 3, 2018, 2 pages. (2018).
Halevy et al., "Dead sea bath salt for the treatment of psoriasis vulgaris: a double-blind controlled study", Journal of the European Academy of Dermatology and Venereology, 1997, vol. 9, pp. 237-242.
Katz et al., "Scientific Evidence of the Therapeutic Effects of Dead Sea Treatments: A Systemic Review", Semin Arthritis Rheum, 2012, vol. 42, pp. 186-200.
Khlaifat et al., "Physical and chemical characterization of Dead Sea mud". Materials Characterization, 2010, vol. 61, pp. 564-568.
Kim et al., "Symptoms of atopic dermatitis are influenced by outdoor pollution", J. Allergy. Clin. Immunol., 2013, vol. 132, pp. 495-497.
Kramer et al., "Eczema, respiratory allergies, and traffic-related air pollution in birth cohorts from small-town areas", J Dermatol. Sci., 2009, vol. 56, pp. 99-105.
Krutmann et al., "Pollution and skin: From epidemiological and mechanistic studies to clinical implications", Journal of Dermatological Science, 2014, vol. 76, pp. 163-168.
Larrieu et al., "Are the Short-term Effects of Air Pollution Restricted to Cardiorespiratory Diseases?", Am. J. Epidemiol., 2009, vol. 169, pp. 1201-1208.
Lu et al., "Assessment of metals pollution and health risk in dust from nursery schools in Xi'an, China", Environ. Res., 2014, vol. 128, pp. 27-34.
Ma'Or et al., "Skin smoothing effects of Dead Sea minerals: comparative profilometric evaluation of skin surface", International Journal of Cosmetic Science, 1997, vol. 19, pp. 105-110.
Moses et al., "The Dead Sea, A Unique Natural Health Resort", IMAJ, 2006, vol. 8, pp. 483-488.

(Continued)

*Primary Examiner* — Melissa S Mercier
*Assistant Examiner* — Caralynne E Helm
(74) *Attorney, Agent, or Firm* — Vorys, Sater, Seymour and Pease LLP; Anthony P. Venturino; Maryellen Feehery Hank

(57) ABSTRACT

Compositions are provided which include at last one Dead Sea extract and at least one polysaccharide, wherein the repeating unit of said polysaccharide is a tetrasaccharide consisting of two D-glucose residues, one L-fucose residue and one D-glucuronic acid residue. Formulations include the compositions which are used as skin protectants against pollution.

6 Claims, 5 Drawing Sheets

(56) References Cited

OTHER PUBLICATIONS

Portugal-Cohen et al., "Antipollution skin protection—a new paradigm and its demonstration on two active compounds", Clinical, Cosmetic and Investigational Dermatology, 2017, vol. 10, pp. 185-193.
Sukenik et al., "Treatment of Psoriatic Arthritis at the Dead Sea", J. Rheumatol., 1994, vol. 21, pp. 1305-1309.
Vierkotter et al., "Airborne Particle Exposure and Extrinsic Skin Aging", J. Invest. Dermatol., 2010, vol. 130, pp. 2719-2726.
Xu et al., "Ambient ozone as a risk factor for skin disorders", Br. J. Dermatol., 2011, vol. 165, pp. 199-228.
Sodium Chloride Specification Sheet (Year: 2010).
Shapley http://butane.chem.uiuc.edu/pshapley/genchem1/I21/1.html (Year: 2011).
Tentative Report from the Cosmetic Ingredient Review 2012 52 pages (Year: 2012).

* cited by examiner

COMPOSITIONS COMPRISING DEAD SEA WATER AND POLYSACCHARIDES AND USES THEREOF AS SKIN PROTECTANTS

FIELD OF THE INVENTION

This invention relates to compositions comprising Dead Sea extract in combination with one or more polysaccharides for use as skin protectants against pollution.

BACKGROUND OF THE INVENTION

The World Health Organization (WHO) defines pollution as contamination of the indoor or outdoor environment by any chemical, physical or biological agent that modifies the natural characteristics of the atmosphere.

The evolution of our lifestyle and the increasing urbanization during the past years amplify the risks associated with pollution, making the pollution one of the major sources of concern for health and beauty.

Air pollution, caused by industry, vehicle fumes, cigarette smoke and other sources together with solar radiation (ultra violet, UV) are known to have a detrimental effect on human skin and body health altogether and lead to various illnesses.

Pollution may be the source of cutaneous stress as pollutants can react with skin, alter skin barrier, penetrate through skin barrier and cause damage such as oxidation and inflammation due to the reaction with the skin cells and other cell bio-molecules therein such as skin proteins, lipids and DNA.

The effect of pollutants on the skin may result with xerotic skin, sensitive skin, premature and accelerated aging of the skin for example wrinkle formation, abnormal pigmentation, skin dryness and more. Pollutants may also be involved in acne and skin cancer.

The negative impact of urban pollution to skin (both healthy skin and skin pathologies) have been discussed in several scientific researches [1]-[6].

Vierkotter et al. illustrated the association between airborne particle exposure and extrinsic skin aging, particularly pigment spot formation [1].

Kim et al. 2013 studied the effect of air pollution on patients with atopic dermatitis. It was demonstrated that outdoor air pollution, including particulate matter (PM), gases and volatile organic compounds (VOCs), may worsen atopic dermatitis and should be controlled when managing these patients [2].

Larrieu et al. found that the risk of developing skin rash increased during the three days following exposure to increases of 10 $mg/m^3$ in PM or ozone levels [3].

Kramer et al. 2010 investigated the relationship between traffic-associated pollution and eczema in children aged 6 years. They found the prevalence was significantly higher in children who lived in traffic-related, highly polluted areas [4].

Xu et al. referred to emergency room visits for skin conditions with ozone exposure [5].

Lu X et al. illustrated that an increase of 10 $mg/m^3$ ozone led to statistically significant increases in urticarial, eczema, contact dermatitis and rash [6].

Sources of pollution can be classified into two types i.e., primary pollutants and secondary pollutants [7].

Primary pollutants include two main groups; particulate matter (PM) and gases [e.g., $CO_2$, $CO$, $SO_2$, $NO$, $NO_2$, and other NOx (nitrogen oxides, such as $N_2O$, $N_2O_2$, $N_2O_3$, $N_2O_4$ and $N_2O_5$)] including light molecular weight hydrocarbons e.g., volatile organic compounds (VOC). The particles may also carry polyaromatic hydrocarbons (PAHs) which are highly lipophilic and easily penetrate the skin. Polychlorinated biphenyls (PCBs) are another toxic PM. The particulate matter plays a major role in primary pollution. It contains toxic organic compounds, heavy metals, driving automobile smoke and burning plants, smoke, dirt and dust from industrial factories, agriculture farming and roads.

Under certain atmospheric conditions secondary pollutants such as ozone and peroxy acetyl nitrates (PANs) are formed from photochemical reactions between the primary pollutants, heat and UV radiation. These pollutants stay low in the atmosphere (troposphere) and settle over both urban and rural areas forming what is typically known as smog.

The level of pollution and pollutant concentration varies throughout the day, by season, geographic location and according to the level of human activity. In particular, ozone levels increase during summer, when the strong sunshine enhances ozone production via photochemical reactions between primary pollutants. Nitrous gases, mainly from automobile combustion and industry are generally higher in South American, Far East Asian big cities and some European cities.

The natural skin ability of self-defense against pollution risks is limited. The main factor in skin protection is the skin integrity and therefore the skin barrier functioning as a frontline shield against penetration of pollutants. However, prolonged and repetitive exposure to high levels of pollutants impairs the skin's natural defense capacity.

Stimulating skin barrier natural defense can be performed either by biologically coping with pollution risks at the long term or through physically creating a film on the skin which function as a secondary barrier, and as such immediately reduces the pollution skin exposure and damage.

Dead Sea water, salts, minerals and mud are well known for their therapeutic efficacy in treating a variety of skin conditions as well as for their cosmetic benefits [8]-[11].

GLYCOFILM® and POLLUSTOP® are commercial names of cosmetic ingredients which comprise an anionic polysaccharide of high molecular weight. The polysaccharide is obtained by biotechnology means and when formulated in a cosmetic preparation serves as a screen against pollution thanks to its ability to form a matrix which serves as a physical barrier to three types of pollution stresses as follows: Atmospheric pollution (carbon particles, PM and heavy metals); Domestic pollution (chemicals); and UV radiation. As such, GLYCOFILM® and POLLUSTOP® limit the extracellular and intercellular damages induced by such pollution stresses e.g., oxidative stress, inflammation and mitochondrial toxicity [12]-[16].

REFERENCES

[1] Vierkotter A, Schikowski T, Ranft U, Sugiri D, Matsui M, Kramer U, et al. *Airborne particle exposure and extrinsic skin aging*. J. Invest Dermatol. 2010, 130, 2719-2726.

[2] Kim J, Kim E H, Oh I, Jung K, Han Y, Cheong H K, et al. *Symptoms of atopic dermatitis are influenced by outdoor pollution*. J. Allergy. Clin. Immunol. 2013, 132, 495-497.

[3] Larrieu S, Lefranc A, Gault G, Chatignoux E, Couvy F, Jouves B, et al. *Are the short-term effects of air pollution restricted to cardiorespiratory diseases*. Am. J. Epidemiol. 2009, 169, 1201-1208.

[4] Kra¨ mer U, Sugiri D, Ranft U, Krutmann J, von Berg A, Berdel D, et al. *Eczema, respiratory allergies, and traffic-* related *air pollution in birth cohorts from small-town areas.* J Dermatol. Sci. 2009, 56, 99-105.
[5] Xu F, Yan S, Wu M, Li F, Xu X, Song W, et al. *Ambient ozone as a risk factor for skin disorders.* Br. J. Dermatol. 2011, 165, 224-225.
[6] Lu X, Zhang X, Li L Y, Chen H. *Assessment of metals pollution and health risk in dust from nursery schools in Xi'an, China.* Environ. Res. 2014, 128, 27-34.
[7] Jean Krutmann et al. *Pollution and skin: From epidemiological and mechanistic studies to clinical implications.* Journal of Dermatological Science 2014, 76, 163-168.
[8] Sukenik S., et al., *Treatment of psoriatic arthritis at the Dead Sea.* J. Rheumatol. 1994, 21, 1305-1309.
[9] S. Halevy, et al. *Dead Sea bath salt for the treatment of psoriasis vulgaris: a double-blind controlled study.* Journal of the European Academy of Dermatology and Venereology, 1997, 9, 237-242.
[10] Maor Z. and Yehuda S. *Skin smoothing effects of Dead Sea minerals: comparative profilometric evaluation of skin surface.* International Journal of Cosmetic Science, 1997, 19, 105-110.
[11] Shimon W. Moses, Michael David, Ehud Goldhammer, Asher Tal and Shaul Sukenik. *The Dead Sea, A Unique Natural Health Resort.* IMAJ, 2006, 8, 483-488.
[12] U.S. Pat. No. 4,638,059
[13] FR 2837097
[14] FR 2837388
[15] FR 2856925
[16] GLYCOFILM® and POLLUSTOP®: aston-chemicals.com/news/2015/10/18/POLLUSTOP/.

SUMMARY OF THE INVENTION

As the present application will further disclose, combinations which comprise a natural extract from the Dead Sea and at least one polysaccharide with specific characteristics (e.g., found in the commercially available products POLLUSTOP® and GLYCOFILM®) have shown protective activity against environmental pollutants.

Specifically, the inventors of the present disclosure have surprisingly found that combinations of Dead Sea extract and at least one specific polysaccharide provide skin protection against various pollutants. In particular, the inventors have found that while solutions of Dead Sea extract alone and solutions of the specific polysaccharide alone did not provide any effect against pollution caused due to exposure of skin tissues to ozone, compositions with both the Dead Sea extract and the specific polysaccharide illustrated a significant efficient protection against ozone. The inventors have found that the inflammation effect induced by exposure of skin tissues to ozone levels has been significantly reduced when these tissues were treated with the combination of the Dead Sea extract and the specific polysaccharide according to the present disclosure.

Further, the inventors of the present disclosure have surprisingly found that solutions of Dead Sea extract alone have protective effect against skin exposure to a mixture of heavy metals and atmospheric particulate materials which are known as inducing skin pollution stress. Similarly, as expected, compositions comprising the specific polysaccharide of POLLUSTOP® illustrated a protective effect against exposure to mixture of heavy metals and atmospheric particulate materials on reconstructed epidermis. This protection activity was retained with compositions which comprised a combination of the Dead Sea extract and the specific polysaccharide of POLLUSTOP®.

Dead Sea ingredients are known for their beneficial therapeutic and cosmetic uses. The present invention provides compositions with Dead Sea extracts together with polysaccharides, the latter are known of their protective properties against specific pollution stress. The present invention provides compositions which not only retain the healing and cosmetic properties of Dead Sea extracts but also provide unique characteristics as skin protectants against polluting agents, in particular against ozone, which may be a dominant effector, damaging skin health and may even be fatal to the human body and skin.

It is noted that the level of pollution and pollutants concentrations may vary throughout the day, by season, geographic location and according to the level of human activity. Thus, the compositions of the present disclosure may be used at various concentrations and at various ratios (e.g., molar, weight) between the active components (i.e., Dead Sea extract and polysaccharide) and as such may provide selective and/or controlled protection against specific pollutants as a function of the amount and/or the distribution of the latter.

Thus, in one of its aspects, the present invention provides a composition comprising at least one Dead Sea extract and at least one polysaccharide, wherein the repeating unit of the polysaccharide is a tetrasaccharide consisting of two D-glucose residues, one L-fucose residue and one D-glucuronic acid residue.

In another one of its aspects the present invention provides a composition according to the invention for use as skin protectant against pollution (e.g., atmospheric pollution, domestic pollution and UV related pollution).

In a further one of its aspects the present invention provides a use of the composition according to the invention for the manufacture of a formulation (and/or an article comprising same e.g., a patch) for protecting skin against pollution.

In yet another one of its aspects the present invention provides a composition according to the invention for use as skin protectant against at least one pollutant (e.g., atmospheric air pollutant, domestic pollutant, optionally in combination with pollutants formed as a result of UV radiation).

In a further one of its aspects the present invention provides a use of the composition according to the invention for the manufacture of a formulation (and/or an article comprising same e.g., a patch) for protecting skin against at least one pollutant.

Yet, in a further one of its aspects the present invention provides a composition according to the invention for use as skin protectant against at least one pollutant selected from the group consisting of particulate matter/s, heavy metal/s, carbon particle/s, smoke, dirt, dust, organic compound/s, polyaromatic hydrocarbon/s, gas/s, ozone, peroxyacetyl nitrate/s, smog and any combination thereof.

In a further one of its aspects the present invention provides a use of the composition according to the invention for the manufacture of a formulation (and/or an article comprising same e.g., a patch) for protecting skin against at least one pollutant selected from the group consisting of particulate matter/s, heavy metal/s, carbon particle/s, smoke, dirt, dust, organic compound/s, polyaromatic hydrocarbon/s, gas/s, ozone, peroxyacetyl nitrate/s, smog and any combination thereof.

In another one of its aspects the present invention provides a composition according to the invention for use as skin protectant against at least one pollutant selected from the group consisting of particulate matter/s, heavy metal/s, carbon particle/s, smoke, dirt, dust, organic compound/s, polyaromatic hydrocarbon/s, gases and any combination thereof.

In a further one of its aspects the present invention provides a use of the composition according to the invention for the manufacture of a formulation (and/or an article comprising same e.g., a patch) for protecting skin against at least one pollutant selected from the group consisting of particulate matter/s, heavy metal/s, carbon particle/s, smoke, dirt, dust, organic compound/s, polyaromatic hydrocarbon/s, gases and any combination thereof.

In a further one of its aspects the present invention provides a composition according to the invention for use as skin protectant against at least one pollutant selected from the group consisting of particulate matter/s, heavy metal/s, carbon particle/s, smoke, dirt, dust, organic compound/s, polyaromatic hydrocarbon/s and any combination thereof.

In a further one of its aspects the present invention provides a use of the composition according to the invention for the manufacture of a formulation (and/or an article comprising same e.g., a patch) for protecting skin against at least one pollutant selected from the group consisting of particulate matter/s, heavy metal/s, carbon particle/s, smoke, dirt, dust, organic compound/s, polyaromatic hydrocarbon/s and any combination thereof.

In yet a further one of its aspects the present invention provides a composition according to the invention for use as skin protectant against at least one pollutant selected from the group consisting of particulate matter/s and heavy metal/s.

In a further one of its aspects the present invention provides a use of the composition according to the invention for the manufacture of a formulation (and/or an article comprising same e.g., a patch) for protecting skin against at least one pollutant selected from the group consisting of particulate matter/s and heavy metal/s.

In another one of its aspects the present invention provides a composition according to the invention for use as skin protectant against at least one pollutant selected from the group consisting of ozone, peroxyacetyl nitrate/s, smog and any combination thereof.

In a further one of its aspects the present invention provides a use of the composition according to the invention for the manufacture of a formulation (and/or an article comprising same e.g., a patch) for protecting skin against at least one pollutant selected from the group consisting of ozone, peroxyacetyl nitrate/s, smog and any combination thereof.

In a further one of its aspects the present invention provides a composition according to the invention for use as skin protectant against ozone.

In a further one of its aspects the present invention provides a use of the composition according to the invention for the manufacture of a formulation (and/or an article comprising same e.g., a patch) for protecting skin against ozone.

Yet, in a further one of its aspects the present invention provides a composition according to the invention for preventing and/or treating at least one disease or disorder of the skin of a subject, said disease or disorder being associate with and/or being induced by pollution (e.g., by one or more polluting agents).

In a further one of its aspects the present invention provides a use of the composition according to the invention for the manufacture of a formulation (and/or an article comprising same e.g., a patch) for preventing and/or treating at least one disease or disorder of the skin of a subject, said disease or disorder being associate with and/or being induced by pollution (e.g., by one or more polluting agents).

In a further one of its aspects the present invention provides a method for protecting the skin of a subject against pollution, the method comprises topical application of the composition (or any formulation thereof) according to the invention onto (at least a region of) the skin of the subject.

In another one of its aspects the present invention provides a method for protecting the skin of a subject against at least one pollutant, the method comprises topical application of the composition (or any formulation thereof) according to the invention onto (at least a region of) the skin of the subject.

In a further one of its aspects the present invention provides a method for selectively protecting the skin of a subject against at least one pollutant (at times two or more pollutants), the method comprises topical application of the composition (or any formulation thereof) according to the invention onto (at least a region of) the skin of the subject.

In a further one of its aspects the present invention provides a method for treating and/or preventing at least one disease or disorder of the skin of a subject, wherein the disease or disorder being associate with and/or being induced by pollution (e.g., by one or more pollutants), the method comprises topical application of the composition (or any formulation thereof) according to the invention onto (at least a region of) the skin of the subject.

Yet, in another one of its aspects, the present invention provides a serum, a lotion, an ointment, a gel, a shampoo, a moisturizer, a sunscreen, a cream, a stick, a spray, an aerosol, foam, a paste, a mousse, a solid, semi-solid, or a liquid make-up, a foundation, or a make-up comprising the composition according to the invention.

In a further one of its aspects, the present invention provides a patch comprising the composition according to the invention.

In another one of its aspects, the present invention provides a use of the composition according to the invention for the preparation of a composition/formulation, the composition/formulation being selected from a cosmetic, skin-care, dermatological or a pharmaceutical composition/formulation.

In yet a further one of its aspects, the present invention provides a use of the composition according to the invention for the preparation of a patch.

In another one of its aspects the present invention provides compositions for use as herein described and exemplified.

BRIEF DESCRIPTION OF THE FIGURES

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
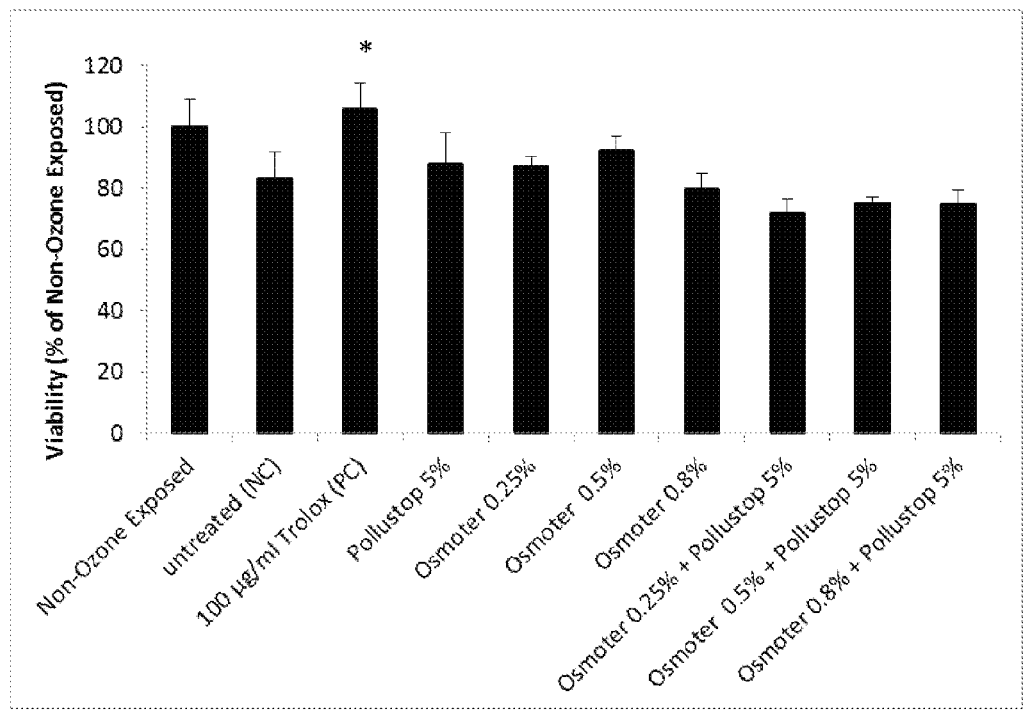
FIG. 1 demonstrates epidermal viability following exposure to ozone, as observed with samples treated with compositions of Dead Sea extract (at various concentrations), POLLUSTOP® and combination of Dead Sea extract and POLLUSTOP®, according to some embodiments of the invention.

The present invention provides in one of its aspects a composition comprising at least one Dead Sea extract and at least one polysaccharide, wherein the repeating unit of the polysaccharide is a tetrasaccharide consisting of two D-glucose residues, one L-fucose residue and one D-glucuronic acid residue.

As used herein the term "Dead Sea extract" refers to one or more natural material, in the form of a single material (e.g., inorganic, organic, salt, etc.) or a mixture of natural materials obtained from the waters of the Dead Sea, the mud surrounding the Dead Sea and/or the soil bed of the Dead Sea.

In some embodiments, the Dead Sea extract is the Dead Sea water. As used herein the term "Dead Sea water" (herein abbreviated DSW) refers to the saline waters obtained from the Dead Sea (Israel or Jordan) region or an aqueous solution prepared by dissolving Dead Sea minerals in an aqueous medium. The term also encompasses aqueous solutions which simulate such natural solution, namely having at least one parameter substantially identical to that measured for the natural DSW, said parameter being at least one of salt content, salt concentration, concentration of a particular cation or anion, ratio of divalent cations to monovalent cations, TDS (Total Dissolved Salt, w/v), soluble natural substances, and other parameters known to define or characterize natural DSW.

In some embodiments, the Dead Sea water having:
1. a specific density of 1.25-1.35 g/ml,
2. pH=4.6-5.6 (at 25° C.), and/or
3. less than 100 cfu/g of non-pathogenic microbes.

In some further embodiments, the DSW is a clear colorless viscous liquid (at 25° C.).

The Dead Sea water having the above physical characteristics is a concentrated extract of Dead Sea Water comprising (among other metal salt ions) $Ca^{+2}$, $Mg^{+2}$, $Na^+$ and $K^+$ and high concentrations of anions such as $Cl^-$ and $Br^-$.

In some embodiments, the concentrations of these ions are, as assessed by a water analysis carried out by the Geological Survey of Israel:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 1800-3200 mg/L
Potassium ($K^+$): 2,500 mg/L, and
Bromide ($Br^-$): 10,000-12,000 mg/L.
Other minerals may also exist in the waters.

In some embodiments, the Dead Sea Water comprises:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 2400-3200 mg/L
Potassium ($K^+$): 2,500 mg/L, and
Bromide ($Br^-$): 10,000-12,000 mg/L.
Other minerals may also exist in the waters.

In some embodiments, the Dead Sea Water comprises:
Calcium ($Ca^{+2}$): 5,000-10,000 mg/L
Chloride ($Cl^-$): 315,000-360,000 mg/L
Magnesium ($Mg^{+2}$): 100,000-150,000 mg/L
Sodium ($Na^+$): 1800-2200 mg/L
Potassium ($K^+$): 1,000-2,000 mg/L, and
Bromide ($Br^-$): 5,000-10,000 mg/L.
Other minerals may also exist in the waters.

In some further embodiments, the Dead Sea Water comprises:
Calcium ($Ca^{+2}$) 34,000-40,000 mg/L
Chloride ($Cl^-$) 320,000-370,000 mg/L
Magnesium ($Mg^{+2}$) 90,000-95,000 mg/L
Potassium ($K^+$) 1,300-2,200 mg/L
Sodium ($Na^+$) 1,500-2,800 mg/L
Bromide ($Br^-$) 11,000-15,000 mg/L.
Other minerals may also exist in the waters.

In some embodiments, the Dead Sea Water comprises:
Calcium ($Ca^{+2}$): 38,000 mg/L
Chloride ($Cl^-$): 345,000 mg/L
Magnesium ($Mg^{+2}$): 92,500 mg/L
Sodium ($Na^+$): 2000 mg/L
Strontium ($Sr^{+2}$): 800 mg/L
Potassium ($K^+$): 1,400 mg/L, and
Bromide ($Br^-$): 11,500 mg/L.
Other minerals may also exist in the waters.

In some embodiments, the DSW is natural DSW which has undergone pre-treatment, e.g., having been concentrated by allowing water to evaporate, for example through solar evaporation, thereafter reconstituted to afford a solution.

In some embodiments the Dead Sea extract is selected from one or more natural material, in the form of a single material or a mixture of natural materials obtained from the waters of the Dead Sea and/or the mud surrounding the Dead Sea and/or the soil bed of the Dead Sea.

In some embodiments the Dead Sea extract is Dead Sea water.

In some embodiments the Dead Sea extract is Dead Sea Water preparation commercially available as "Maris Sa" or "Maris Aqua" (AHAVA, Israel) referred to herein below also as "Osmoter".

In some embodiments the polysaccharide is an anionic polysaccharide.

In some embodiments the polysaccharide is a branched polysaccharide.

In some embodiments the repeating unit of the polysaccharide has the following Formula (I):

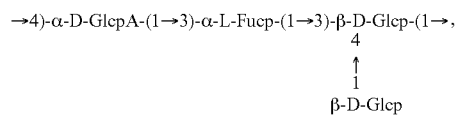

Formula (I)

wherein D-GlcpA designates a D-glucuronic acid residue, L-Fucp designates a L-fucose residue and D-Glcp designates a D-glucose residue.

In some embodiments the repeating unit of the polysaccharide is repeated between about 2500 to about 3500 times in said polysaccharide.

In some embodiments the polysaccharide is totally deacetylated (including the repeating unit).

In some embodiments the polysaccharide may be secreted by *Enterobacter*, gram *bacillus*, deposited under No. NCIB 11870 at the National Collection of Industria Bacteria (Aberdeen, Scotland).

In some embodiments the polysaccharide is the fermentation product of the *Enterobacter, bacillus* gram, filed under No. NCIB 11870.

In some embodiments the molar ratio of D-glucose, L-fucose and D-glucuronic acid of the polysaccharide is about 3:1:1.

In some embodiments the polysaccharide may be secreted by *Klebsiella aerogenes*, Type 54, strain A3, deposited under number ATCC 12657 and 12658.

In some embodiments the molar ratio of D-glucose, L-fucose and D-glucuronic acid is approximately 2:1:1.

In some embodiments the polysaccharide is the fermentation product of *Klebsiella aerogenes*, Type 54, strain A3, deposited under numbers ATCC 12657 and 12658.

In some embodiments the polysaccharide is biodegradable.

In some embodiments the polysaccharide has a molecular weight of about 2000 kDa.

In some embodiments the polysaccharide is Biosaccharide gum-4.

In some embodiments the composition comprises the polysaccharide from the commercially available product POLLUSTOP® (the polysaccharides of POLLUSTOP® and formulations thereof are obtained according to known procedures as disclosed in publications [12] to [15], the content of these publications and the publications disclosed therein are incorporated herein by reference).

In some embodiments, e.g., in case of POLLUSTOP®, the composition may further comprise 1,2-Hexanediol. In some embodiments the composition is preservative free.

In some embodiments the composition according to the present invention comprises the polysaccharide from the commercial available product GLYCOFILM®. To this end, the composition may further comprise phenoxyethanol.

In some embodiments the polysaccharide is an anionic branched polysaccharide having a repeating unit of the following Formula (I):

Formula (I)

→4)-α-D-GlcpA-(1→3)-α-L-Fucp-(1→3)-β-D-Glcp-(1→,
                              4
                              ↑
                              1
                           β-D-Glcp wherein D-GlcpA designates a D-glucuronic acid residue, L-Fucp designates a L-fucose residue and D-Glcp designates a D-glucose residue, and having a molecular weight of about 2000 kDa.

In some embodiments the polysaccharide may be present in the composition at a concentration of between about 0.5% (w/w) to about 5% (w/w), at times at a concentration of between about 1% (w/w) to about 5% (w/w). It is noted that the w/w % is to be understood as the weight % of the polysaccharide out of the total weight of the composition. Same is true when referring to a formulation according to the invention.

In some embodiments the polysaccharide may be present in the composition at a concentration of about 0.5% (w/w).

In some embodiments the polysaccharide may be present in the composition at a concentration of about 1% (w/w).

In some embodiments the polysaccharide may be present in the composition at a concentration of about 2% (w/w).

In some embodiments the polysaccharide may be present in the composition at a concentration of about 3% (w/w).

In some embodiments the polysaccharide may be present in the composition at a concentration of about 4% (w/w).

In some embodiments the polysaccharide may be present in the composition at a concentration of about 5% (w/w).

Intermediate values of the above weight percentages are also within the scope of the present disclosure e.g., 1.5, 2.5, 3.5, 4.5% (w/w) etc.

In some embodiments the Dead Sea extract (e.g., Maris Sal) is present in said composition at a concentration of between about 0.1% to about 2.5% (w/w), at times at a concentration of between about 0.25% to about 2.5% (w/w). It is noted that the w/w % is to be understood as the weight % of the Dead Sea extract out of the total weight of the composition. Same is true when referring to a formulation according to the invention.

In some embodiments the Dead Sea extract may be present in the composition at a concentration of about 0.1% (w/w).

In some embodiments the Dead Sea extract may be present in the composition at a concentration of about 0.25% (w/w).

In some embodiments the Dead Sea extract may be present in the composition at a concentration of about 0.5% (w/w).

In some embodiments the Dead Sea extract may be present in the composition at a concentration of about 0.8% (w/w).

In some embodiments the Dead Sea extract may be present in the composition at a concentration of about 1% (w/w).

In some embodiments the Dead Sea extract may be present in the composition at a concentration of about 1.5% (w/w).

In some embodiments the Dead Sea extract may be present in the composition at a concentration of about 2% (w/w).

In some embodiments the Dead Sea extract may be present in the composition at a concentration of about 2.4% (w/w).

In some embodiments the Dead Sea extract may be present in the composition at a concentration of about 2.5% (w/w).

In some embodiments polysaccharide may be present in the composition at a concentration of about 5% (w/w) and the Dead Sea extract may be present in the composition at a concentration of between about 0.25% to about 0.8% (w/w) of the total weight of the composition.

In some embodiments polysaccharide may present in the composition at a concentration of about 5% (w/w) and the Dead Sea extract may be present in the composition at a concentration of between about 0.25% of the total weight of the composition.

In some embodiments polysaccharide may present in the composition at a concentration of about 5% (w/w) and the Dead Sea extract may be present in the composition at a concentration of between about 0.8% of the total weight of the composition.

As used herein above and below the term "about" refers to 10% of the indicated value.

In some embodiments the composition according to the invention may further comprise at least one alcohol (e.g., ethanol, 2-propanol, 1-propanol, methanol). To this end, the alcohol may be used for the formulation of the composition into a gel as disclosed in [12]-[14] which content thereof in this respect is fully incorporated herein by reference.

In some embodiments the composition according to the invention may further comprise at least one gelling agent e.g., glycol.

In some embodiments the composition according to the invention may further comprise glycerin.

In some embodiments, the composition of the present invention is a topical composition.

In some embodiments, the composition of the present invention is a cosmetic composition.

In some embodiments, the composition of the present invention is a pharmaceutical composition. In further embodiments, the pharmaceutical composition is for topical application (i.e., topical composition).

The compositions of the present invention may be made into a wide variety of product forms (e.g., formulations) suitable for, e.g., topical administration/application onto the skin of a subject. Non-limiting examples are a serum, a lotion, an ointment, a gel, a cream, a water in oil or oil in water emulsion, a shampoo, a moisturizer, a sunscreen, a cream, a stick, a spray, an aerosol, foam, a paste, a mousse, a solid, semi-solid, or a liquid make-up, a foundation, and a make-up. A variety of cosmetics or skin-care formulations including solid, semi-solid, or a liquid make-up such as foundations, eye make-up etc. are also encompassed by the present disclosure.

Thus, in another one of its aspects the present invention provides a serum, a lotion, an ointment, a gel, a shampoo, a moisturizer, a sunscreen, a cream, a stick, a spray, an aerosol, foam, a paste, a mousse, a solid, semi-solid, or a liquid make-up, a foundation, or a make-up comprising the composition according to the invention.

In some embodiments, the composition of the invention is formulated as a lotion.

In some embodiments, the composition of the invention is formulated as a serum.

In some embodiments, the composition of the invention is formulated as a gel.

In some embodiments, the composition of the invention is formulated as a film.

In some embodiments the composition of the invention is a film forming formulation.

In some embodiments, the composition may be formulated as a personal skin care product. In some embodiments the personal skin care product may be selected from a cleansing product or a moisturizing product. In some embodiments the cleansing product may be selected from a liquid soap, a bath gel or a shower gel. In some embodiments the moisturizing product may be selected from a cream, a lotion, a gel-cream, a serum, a facial mask, a conditioner or a mask.

In some embodiments the personal skin care product is a facial skin product for example a cream, a gel, a mask, a serum, a lotion, a makeup and the like.

In some embodiments the personal skin care product is an eye skin care product.

In some embodiments the personal skin care product is a body care product.

The viscosity of the compositions of the invention or any formulations thereof may vary depending on the form (i.e., lotion, serum, cream, gel, film etc.), concentration of the active combination (i.e., Dead Sea extract and polysaccharide), the carrier, the purpose (i.e., cosmetic or therapeutic), end user and other parameters.

In some embodiments, the composition is formulated in water in oil (W/O) emulsion.

In some embodiments, the compositions of the present invention may be formulated as a dermatological formulation. In some embodiments the dermatological formulation may be a pharmaceutical or a cosmetic formulation. In some embodiments the formulation may comprise at least one drug molecule.

The compositions according to the present invention (cosmetic or therapeutic) may comprise at least one dermatological, cosmetically or pharmaceutically acceptable additive selected amongst inert and effect-inducing additives. In some embodiments, the inert additive is selected from a diluent, a preservative, an abrasive, an anti-caking agent, an antistatic agent, a binder, a buffer, a dispersant, an emollient, an emulsifier, a co-emulsifiers, a fibrous material, a film forming agent, a fixative, a foaming agent, a foam stabilizer, a foam booster, a gallant, a lubricant, a moisture barrier agent, an opacifier, a plasticizer, a preservative, a propellant, a stabilizer a surfactant, a suspending agent, a thickener, a wetting agent, a film former, a liquefier or any combination of the same.

In still some embodiments, the inert additive may be an emollient, being selected from one or more of vegetable and animal fats, silicones and oils such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, *Chamomilla recutita* (*matricaria*) flower oil, *Hypericum perforatum* oil, soybean oil and *Vitis vinifera* (grape) seed oil; acetoglyceride esters, such as acetylated monoglycerides; alkyl esters of fatty acids having 10 to 24 carbon atoms which include, but are not limited to, methyl, isopropyl, and butyl esters of fatty acids such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; vegetable waxes including, but not limited to, caranuba and candelilla waxes; surface active silicone derivatives such as cyclopentasiloxane PEG/PPG-18/18 dimethicone, dimethicone, dimethicone crosspolymer, cyclomethicone, cyclomethicone & dimethiconol; caprylic/capric triglyceride; cholesterol fatty acid esters; or any mixtures thereof.

In some embodiments, the effect-inducing additive may be selected from one or more of an anti-acne agent, an anti-aging agent, an antibacterial agent, an anti-cellulites agent, an antidandruff agent, an antifungal agent, an anti-inflammatory agent, an anti-irritation agent, an antimicrobial agent, an antioxidant, an antiperspirant agent, an antiseptic agent, a cell stimulant, a cleansing agent, a conditioner, a deodorant, a fragrance ingredient, a depilatory, a detergent, an enzyme, an essential oil, an exfoliant, a fungicide, a glosser, hair conditioner (hair conditioner agent), hair set resin, hair sheen agent, hair waving agent, a humectants, a moisturizer, an ointment base, a perfume, a protein, a skin calming agent, a skin cleanser, a skin conditioner (skin conditioning agent), a skin healing agent, a skin lightening agent, a skin protectant, a skin smoothing agent, a skin softening agent, a skin soothing agent, a sunscreen agent, a tanning accelerator, vitamins, a colorant, a flavoring agent or any combination thereof.

In some embodiments, the at least one additive is a sunscreen.

In another one of its aspects the present invention provides a patch (e.g., cosmetic or pharmaceutical, particularly dermatological) comprising the composition according to the invention.

In yet a further one of its aspects, the present invention provides a use of the composition according to the invention for the preparation of a patch.

The cosmetic or pharmaceutical compositions/formulations of the present invention may also comprise pharmaceutical actives useful in the form of a chemical substance, material or compound, e.g., suitable for topical administration, to induce a desired local or systemic effect. Non-limiting examples of such actives are an antibiotic, an antiviral agent, an analgesic (e.g. ibuprofen, acetyl salicylic acid, naproxen, and the like), an antihistamine, an anti-inflammatory agent, an antipruritic, an antipyretic, an anesthetic agent, a diagnostic agent, a hormone, an antifungal agent, an antimicrobial agent, a cutaneous growth enhancer, a pigment modulator, an antiproliferative, an antipsoriatic, a retinoid, an anti-acne medicament (e.g. benzoyl peroxide, sulfur, and the like), an antineoplastic agent, a phototherapeutic agent, a keratolys (e.g. resorcinol, salicylic acid, and the like) and mixtures thereof.

Application of a composition of the invention onto the skin of a subject, for cosmetic/skin-care or therapeutic purposes may be in a single dose, in multiple doses, in a continuous or intermittent manner, depending, for example, upon the subject's physiological condition, whether the purpose of the administration is cosmetic or therapeutic/prophylactic and other factors known to the medical practitioner. The application of a composition of the invention may be essentially continuous over a pre-selected period of time or may be in a series of spaced doses.

Further, as the level of pollution and pollutant concentrations may vary throughout the time of the day, the compositions/formulations of the present invention may be for use overnight and/or during the day. The application amount and frequency may depend from the severity/amount of pollution during the day/night as well as the geographic location of the subject.

The compositions of the present invention are typically prepared by combining the Dead Sea extract/s and polysaccharide/s in appropriate concentrations. Other active or inert additives selected by one of skill in the art can optionally be added.

In some embodiments, to achieve selective protection against one or more, two or more, three or more pollutants etc., the concentrations of the Dead Sea extract and the polysaccharide in the compositions according to the present invention may be adjusted/optimized (e.g., to reach the effective amounts thereof) to achieve the required protection. Topical administration routes and frequencies may also be adjusted for controlled protection against various types of pollutants.

The compositions of the present invention, being substantially for topical use, may be a skin-care formulation or a therapeutic formulation.

In some embodiments, the compositions of the present invention are skin-care or dermo-pharmaceutical compositions (including, e.g., toiletries, health and beauty aids and cosmeceuticals) used for cosmetic and personal skin-care applications. The term "cosmetic composition" or "skin care compostion" relates to a composition of the invention that can be used for cosmetic purposes, purposes of hygiene or skin-care or as a basis for delivery of one or more pharmaceutical ingredients. It is also possible that these compositions are used for two or more of these same purposes at one time. For example, a medicated dandruff shampoo may be used as a personal care product, i.e., to provide clean hair (e.g., to remove pollutants from same), and at the same time have pharmacological properties.

In some embodiments, the cosmetic compositions are for promoting bodily attractiveness, cover or mask the physical manifestations of a disorder or disease, modulate or alleviate wrinkling, photo-damage, unevenness and dryness in the skin of a mammal. The compositions additionally regulate skin condition and signs of skin aging (all perceptible manifestations as well as any other macro or micro effects) by regulating visible and/or tactile discontinuities in skin texture, including fine lines, wrinkles, enlarged pores, roughness and other skin texture discontinuities associated with aged skin with reduced irritation and dryness.

Thus, the invention further provides a use of the composition according to the invention for the preparation of a composition/formulation, the composition/formulation being selected from a cosmetic, skin-care, dermatological and a pharmaceutical composition/formulation.

In some embodiments, in addition to the skin-care and/or dermo-pharmaceutical purposes, the compositions according to the invention further provide protection against pollution e.g., skin protection.

In another one of its aspects the present invention provides a composition according the invention, for use as skin protectant against pollution.

In some embodiments, the present invention provides a composition according to the invention for use as skin protectant against at least one pollutant.

In some embodiments, the skin protectant effect of the compositions according to the invention may be selective against a particular pollutant or against a combination of one or more pollutants, at times against a combination of two or more pollutants.

In some embodiments skin protection against pollution may be envisaged as improving skin barrier function e.g., by physically shielding the skin.

In some embodiments skin protection against pollution may be envisaged as scavenging (e.g., deactivating) the oxidative pollutants.

In some embodiments skin protection against pollution may be one or both of biological and physical defense.

In some embodiments skin protection against pollution may by short term protection (e.g., by topical application that provides physical shield against exposure to pollutants) and/or long term exposure to pollution (e.g., by continuous topical application that negate the pollution detrimental accumulated damage to the skin which may result with one or more skin diseases, disorders and/or skin imperfection).

As used herein the term "pollution" or any lingual variation thereof is envisaged as any contamination of the indoor or outdoor environment by any chemical, physical or biological agent that modifies the natural characteristics of the atmosphere. Non-limiting examples of pollution are air pollution caused by industry, vehicle fumes, cigarette smoke and other sources, optionally in combination with solar radiation. Dust (e.g., desert dust) as well as water pollution caused by industrial sewage, agricultural biocides and floods are further non-limiting examples of pollution. The pollution may be one or more of atmospheric pollution, domestic pollution and UV pollution (e.g., induced by UV solar radiation).

Provided herein below are non-limiting examples of pollutants: particulate matter [e.g., fine particles (PM 2.5) and coarse particles (PM 10)]; gases such as $CO_2$, CO, $SO_2$, NO, $NO_2$, and other NOx (nitrogen oxides, such as $N_2O$, $N_2O_2$, $N_2O_3$, $N_2O_4$ and $N_2O_5$)], including light molecular weight hydrocarbons e.g., volatile organic compounds (VOC); polyaromatic hydrocarbons (PAHs) carried by pollutant particles; organic compounds; heavy metals; driving automobile smoke; burning plants; smoke; dirt and dust e.g., from factories, farming and roads; desert dust; urban dust; ozone; peroxy acetyl nitrates (PANs); and smog. Other pollutants known in the art are also within the scope of the present disclosure e.g., polychlorinated biphenyls (PCBs).

As illustrated herein below, skin protection against mixture of pollutants containing heavy metals and atmospheric PM has been demonstrated for Dead Sea extract alone and for the polysaccharide alone. Protection of the individual components (i.e., Dead Sea extract and polysaccharide) against exposure to ozone has not be demonstrated. Only their combination was effective against exposure to ozone.

Thus, in some embodiments the compositions of the present invention which comprise both Dead Sea extract and polysaccharide may provide broad protection against different types of pollutants (e.g., protection against more than one pollutant, at times more than two pollutants, at time more than three pollutants etc.).

In some embodiments the compositions according to the present invention may provide protection against at least one primary pollutant.

In some embodiments the compositions according to the present invention may provide protection against at least one secondary pollutant.

In some embodiments the compositions according to the present invention may provide protection against at least one primary pollutant and at least one secondary pollutant.

In some embodiments the compositions according to the present invention provide protection against a mixture of pollutants containing heavy metals and atmospheric PM.

In some embodiments the compositions according to the invention provide protection against ozone and a mixture of pollutants containing heavy metals and atmospheric PM.

In a further one of its aspects the present invention provides a composition according to the invention for use as skin protectant against at least one pollutant wherein said at least one pollutant is selected from the group consisting of particulate matter/s, heavy metal/s, carbon particle/s, smoke, dirt, dust, organic compound/s, polyaromatic hydrocarbon/s (e.g., carried by particulate matter), gas/s, ozone, peroxyacetyl nitrate/s, smog and any combination thereof.

In some embodiments the heavy metal is selected from the group consisting of As, Cd, Co, Cr, Ni, Pb, Sr, Sb and any combination thereof (optionally in the form of an alloy).

In some embodiments the gas is selected from the group consisting of $CO_2$, CO, $SO_2$, NO, $NO_2$, $N_2O$, $N_2O_2$, $N_2O_3$, $N_2O_4$, $N_2O_5$, light molecular weight hydrocarbons (e.g., volatile organic compounds) and any combination thereof.

In some embodiment the at least one pollutant is selected from the group consisting of particulate matter/s, heavy metal/s, carbon particle/s, smoke, dirt, dust, organic compound/s, polyaromatic hydrocarbon/s, gases and any combination thereof.

In some embodiments the at least one pollutant is selected from the group consisting of particulate matter/s, heavy metal/s, carbon particle/s, smoke, dirt, dust, organic compound/s, polyaromatic hydrocarbon/s and any combination thereof.

In some embodiments the at least one pollutant is selected from the group consisting of particulate matter/s and heavy metal/s.

In some embodiments the at least one pollutant is selected from the group consisting of ozone, peroxyacetyl nitrate/s, smog and any combination thereof.

In some embodiments the at least one pollutant is ozone.

In some embodiments the at least one pollutant is selected from the group consisting of at least one particulate matter, at least one heavy metal and ozone.

The protective effect against pollution of the compositions/formulations according to the present invention provides them with the benefit of protecting the skin of subject from diseases or disorders of the skin associated with pollution.

Thus, in another one of its aspects the present invention provides the compositions according to the invention for preventing and/or treating at least one disease or disorder of the skin of a subject, the disease or disorder being associate with and/or being induced by pollution.

In another one of its aspects the present invention provides the compositions according to the invention for preventing and/or treating at least one disease or disorder of the skin of a subject, the disease or disorder being associate with and/or being induced by pollution, optionally in combination with exposure to the sun and/or UV radiation.

In another one of its aspects the present invention provides the compositions according to the invention for preventing and/or treating at least one disease or disorder of the skin of a subject, the disease or disorder being associate with and/or being induced by pollution, optionally in combination with exposure to infrared (IR) or other electromagnetic radiation.

In some embodiments the disease or disorder of the skin may be related to inflammation.

In some embodiments the disease or disorder of the skin may be related to oxidation.

In some embodiments the disease or disorder of the skin may be related to one or both of hypoxia and anoxia.

In some embodiments the disease or disorder of the skin may be related to malfunctioning of one or both of gene transcription and translation.

In some embodiments the disease or disorder of the skin may be related to one or both of abnormal protein and enzymatic folding and/or functioning.

In some embodiments the disease or disorder (e.g., pathology) of the skin is selected from the group consisting of dry skin, sensitive skin, irritated skin, diabetic skin, photo damaged skin, psoriatic skin, atopic skin, contact dermatitis skin, rosacea skin, premature aged skin, accelerated skin aging (e.g., wrinkle formation), skin abnormal pigmentation, acne, cancer and any combinations thereof.

In another one of its aspects the present invention provides a method for protecting the skin of a subject against at least one pollutant, the method comprises applying to the skin of the subject a composition according to the invention (or any formulation thereof).

In some embodiments the at least one pollutant is selected from the group consisting of particulate matter/s, heavy metal/s, carbon particle/s, smoke, dirt, dust, organic compound/s, polyaromatic hydrocarbon/s, gas/s, ozone, peroxyacetyl nitrate/s, smog and any combination thereof.

In some embodiments the heavy metal is selected from the group consisting of As, Cd, Co, Cr, Ni, Pb, Sr, Sb and any combination thereof.

In some embodiments the gas is selected from the group consisting of $CO_2$, CO, $SO_2$, NO, $NO_2$, $N_2O$, $N_2O_2$, $N_2O_3$, $N_2O_4$, $N_2O_5$, light molecular weight hydrocarbons (e.g., volatile organic compounds) and any combination thereof.

In some embodiments the at least one pollutant is selected from the group consisting of particulate matter/s, heavy metal/s, carbon particle/s, smoke, dirt, dust, organic compound/s, polyaromatic hydrocarbon/s, gases and any combination thereof.

In some embodiments the at least one pollutant is selected from the group consisting of particulate matter/s, heavy metal/s, carbon particle/s, smoke, dirt, dust, organic compound/s, polyaromatic hydrocarbon/s and any combination thereof.

In some embodiments the at least one pollutant is selected from the group consisting of particulate matter/s and heavy metal/s.

In some embodiments the at least one pollutant is selected from the group consisting of ozone, peroxyacetyl nitrate/s, smog and any combination thereof.

In some embodiments the at least one pollutant is ozone.

In some embodiments, the method for protecting the skin of a subject against at least one pollutant may be selective against a particular pollutant or against a combination of one or more pollutants, or at times may even be selective against a combination of two or more pollutants. To this end, the dosages of the compositions according to the invention (e.g., the concentrations and ratios of the active ingredients in the compositions may be adjusted accordingly as well as the topical application thereof (e.g., duration and/or frequency of application).

In yet a further one of its aspects the present invention provides a method for treating and/or preventing at least one disease or disorder of the skin of a subject, wherein the disease or disorder being associate with and/or being induced by pollution (e.g., by the at least one pollution agent as herein described) (optionally in combination with exposure to the sun and/or UV radiation), the method comprising applying to the skin of the subject a composition according to the invention (or any formulation thereof).

In some embodiments the disease or disorder of the skin is related to inflammation.

In some embodiments the disease or disorder of the skin is related to oxidation.

In some embodiments the disease or disorder of the skin may be related to one or both of hypoxia and anoxia.

In some embodiments the disease or disorder of the skin may be related to malfunctioning of one or both of gene transcription and translation.

In some embodiments the disease or disorder of the skin may be related to one or both of abnormal protein and enzymatic folding and/or functioning.

In some embodiments the disease or disorder of the skin is selected from the group consisting of dry skin, sensitive skin, irritated skin, diabetic skin, photo damaged skin, psoriatic skin, atopic skin, contact dermatitis skin, rosacea skin, acne, premature aged skin, accelerated skin aging (e.g., wrinkle formation), skin abnormal pigmentation, acne, cancer and any combinations thereof.

In a further one of its aspects the present invention provides use of a composition according to the invention in the manufacture of a formulation for the treatment and/or prevention of at least one disease or disorder of the skin of a subject, wherein said disease or disorder being associate with and/or being induced by pollution.

In some embodiments the disease or disorder of the skin is related to inflammation.

In some embodiments the disease or disorder of the skin is related to oxidation.

In some embodiments the disease or disorder of the skin may be related to one or both of hypoxia and anoxia.

In some embodiments the disease or disorder of the skin may be related to malfunctioning of one or both of gene transcription and translation.

In some embodiments the disease or disorder of the skin may be related to one or both of abnormal protein and enzymatic folding and/or functioning.

In some embodiments the disease or disorder of the skin is selected from the group consisting of dry skin, sensitive skin, irritated skin, diabetic skin, photo damaged skin, psoriatic skin, atopic skin, contact dermatitis skin, rosacea skin, acne, premature aged skin, accelerated skin aging (e.g., wrinkle formation), skin abnormal pigmentation, acne, cancer and any combinations thereof.

Without wishing to be bound by theory, the protection properties of the compositions/formulations of the present invention may be by providing physical protection to the skin by forming a shied on the skin surface and as such assist in reducing the pollutants load on the skin e.g., provide a screen against penetration of pollutants to the skin. The compositions of the present invention may also have a curing effect on defected skin (e.g., improving the state of the skin, preventing and/or treating imperfections of the skin, such as dry or dull skin, and other known curing properties of Dead Sea salts and minerals) and as such provide the skin with enhance biological and or physical protection against pollutants.

Thus, in some embodiments the compositions according to the invention may also be used for treating or preventing a disease or disorder of the skin of a subject, the disease or disorder may optionally be related to one or more of age, gender, skin color, skin wounds, acne, exposure to the sun, UV radiation, inflammation, diabetic skin, and pre-existence of a disease not associated with the skin. In some embodiments the disease or disorder of the skin is related to sun exposure or is a secondary condition, being related to an existing condition or inflammation. In some further embodiments the disease or disorder of the skin is age-related. In yet further embodiments the disease or disorder of the skin is selected from a wound, acne, psoriasis, atopic skin, diabetic skin, dermatitis, eczema, xerosis, dry skin, and chaffed skin. It is noted that the treating and/or prevention effect of the compositions of the present invention may provide enhanced protection against pollution.

Non-limiting examples of diseases or disorders of the skin are wounds, acne, psoriasis, atopic skin, diabetic skin, dermatitis, eczema, xerotic, xerosis, dry skin, cancer and chaffed skin.

In some embodiments, the subject is suffering, or has predisposition to suffer, or is one which may be exposed to conditions which increase the chances of suffering from a disease or disorder of the skin, which is optionally (may or may not be) related to one or more of age, gender, skin color, skin wounds, exposure to the sun, UV radiation, inflammation, a pre-existence of a disease not associated with the skin, etc.

In some embodiments according to the present invention the disease or disorder may be one or more of xerotic skin, sensitive skin, premature skin aging and accelerated aging symptoms (e.g., wrinkle formation, abnormal pigmentation and skin dryness).

In some embodiments according to the present invention the disease or disorder may be one or more of acne, eczema, skin rashes and skin cancers.

In some embodiments according to the present invention the disease or disorder may be further involved with intrinsic damage to other organs other than the skin.

The compositions or the formulations of the present invention may be applied onto the skin by any one method known for application of a standard skin preparation (e.g., cream, gel etc.). The application may be for a short period of time, namely the composition in a suitable form (as disclosed herein) is applied topically and then removed for example within a few minutes. Alternatively, the compositions may be applied onto the skin and allowed to remain in contact with the skin over longer periods of time. In some embodiments, the composition may be allowed to remain on the skin overnight. In order to achieve long term effective contact with the skin, the compositions of the invention may be absorbed or loaded onto a carrier which retains its form; such carrier may be a patch, a dressing or a bandage in a form providing sufficient contact with the skin.

Thus, in some embodiments of the invention, the composition may be formulated as a leave on composition e.g., a leave on cream, a leave on serum. In some further embodiments of the invention, the composition may be formulated as a rinse-off composition.

As used herein, a "leave on" (in contrary to "rinse off") composition/formulation refers to a composition/formulation that may be in prolonged contact with the skin and can be applied to a skin region without the need to remove it from the skin (e.g., by wiping or rinsing it off) in any way.

In some embodiments, the leave-on composition/formulation may be adapted to be applied to a skin region and to be left on the skin for a time sufficient to achieve an end result.

For ease of use, the compositions/formulations of the present invention may be formed into a kit or a commercial package and provided along with instructions for use. The compositions/formulations comprised in the kit or in the commercial package may be in a quantity and composition suitable for a short term or long term application, for a generic or specific purpose.

The term "topical" as used herein refers to the application of a composition according to the invention directly onto at least a portion of a subject's skin (human's or non-human's skin) so as to achieve a desired effect, e.g., cosmetic or therapeutic effect, at the site of application e.g., at least a region of the skin (e.g., facial skin). In some embodiments, the desired effect is achieved at the site of application without inducing one or more systemic effects. In some embodiments, the formulation of the invention induces at least a partial systemic effect which contributes to the induction of at least one desired effect.

The term "skin" as used herein refers to any part of the human or animal skin, including the whole surface thereof, eyelashes, eyebrows, hair and nails. In the content of the present disclosure, when the compositions are topically applied onto a skin of a subject it is to be understood that the application is onto at least a portion/region of the skin. In some embodiment the skin is at least a region of the facial skin. In some further embodiments the facial skin is the skin region surrounding the eyes.

The term "treatment" as used herein refers to the topical administration of an effective amount of a composition of the present invention effective to ameliorate undesired symptoms associated with a skin disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

The "effective amount", whether a therapeutically or cosmetically effective amount for purposes described herein is determined by such considerations as may be known in the art. The amount must be effective to achieve one or more of the above desired therapeutic or cosmetic effects, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile, a variety of pharmacological parameters such as half-life on the skin, on undesired side effects, if any, on factors such as age and gender, etc.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

As used herein, the singular form "a", "an" and "the" include plural references unless the context clearly dictates otherwise. For example, the term "an extract" or "at least one extract" may independently include a plurality of extracts, including a variety thereof.

Various embodiments and aspects of the present invention as delineated hereinabove and as claimed in the claims section below find experimental support in the following examples.

DETAILED DESCRIPTION OF EMBODIMENTS

The following examples are not in any way intended to limit the scope of the invention as claimed.

Example 1—Preparation of the Compositions of the Present Disclosure

Dead Sea Extract:

In the present disclosure a commercial preparation of Dead Sea minerals (DSM) referred to herein as "Osmoter" was used. The preparations is also known as "Maris Sal" or "Maris Aqua" (Dead Sea Water, DSW) (Source: Geological Survey—Ministry of National Infrastructures, State of Israel, especially for Ahava-Dead Sea Laboratories CAS #INCI Monograph ID:11089).

The "Osmoter" solution has the following composition:

| Salt normality (N) | | Salt normality (N) | |
|---|---|---|---|
| Na | 0.118 (2.720 g/l) | Rb | $3.5 \times 10^{-6}$ ($<3 \times 10^{-4}$ g/l) |
| K | 0.054 (2.100 g/l) | Sb | $<1.6 \times 10^{-7}$ ($<2 \times 10^{-5}$ g/l) |
| Ca | 0.873 (35.000 g/l) | Sr | $7.6 \times 10^{-3}$ (0.670 g/l) |
| Mg | 3.815 (92.700 g/l) | V | $<7.9 \times 10^{-5}$ ($<0.004$ g/l) |
| Ba | $6.6 \times 10^{-5}$ (0.009 g/l) | Th | $<8.6 \times 10^{-8}$ ($<2 \times 10^{-5}$ g/l) |
| Cd | $<1.8 \times 10^{-7}$ ($<2 \times 10^{-5}$ g/l) | U | $<8.4 \times 10^{-8}$ ($<2 \times 10^{-5}$ g/l) |
| Co | $<3.4 \times 10^{-5}$ ($<0.002$ g/l) | Zn | $<3.06 \times 10^{-5}$ ($<0.002$ g/l) |
| Cu | $<3.15 \times 10^{-5}$ ($<0.004$ g/l) | Cl | 9.75 (346 g/l) |
| Cr | $<3.85 \times 10^{-4}$ ($<0.02$ g/l) | Br | 0.175 (14 g/l) |
| Fe | $<3.58 \times 10^{-5}$ ($<0.002$ g/l) | B | 0.011 (0.120 g/l) |
| Li | $5.76 \times 10^{-3}$ (0.040 g/l) | As | $2.7 \times 10^{-5}$ (0.002 g/l) |
| Mn | $1.82 \times 10^{-4}$ (0.010 g/l) | I | $6.30 \times 10^{-7}$ ($8 \times 10^{-8}$ g/l) |
| Mo | $<1.04 \times 10^{-6}$ ($<10^{-4}$ g/l) | SiO2 | $<3.33 \times 10^{-4}$ ($<0.02$ g/l) |
| Ni | $<3.4 \times 10^{-5}$ ($<0.002$ g/l) | SiO4 | $<2.2 \times 10^{-3}$ ($<0.2$ g/l) |
| Pb | $<9.6 \times 10^{-8}$ ($<2 \times 10^{-5}$) | | |

Solutions comprising Dead Sea Minerals/Water were prepared by dilutions of the "Osmoter" preparation. Various concentrations of the "Osmoter" preparation were used i.e., 0.25%, 0.5% and 0.8% (w/w).

Polysaccharide:

The polysaccharide formulation used was POLLUSTOP®, purchased from Solabia Group, Pantin Cedex, France (INCI name: Biosaccharide gum-4 (and) 1,2-Hexanediol; Product code AC145, preservative free). It is noted that in the formulation the polysaccharide was provided in a form of a gel in which the concentration of the polysaccharide was 96.5% (w/w) and the concentration of the 1,2-Hexanediol was 3.5% (w/w).

The polysaccharide, the preparation thereof and the formulation comprising same were disclosed in U.S. Pat. No. 4,638,059, FR 2837097, FR 2837388, FR 2856925 [12]-[15] and GLYCOFILM® and POLLUSTOP® [16], each of which are incorporated herein by reference.

Preparation of Tested Samples:

Osmoter and POLLUSTOP® were mixed with deionized or inversed osmosis purified water alone or in combination in different concentrations which are detailed in Table 1 below.

It is noted that the percentages of the various ingredients of the compositions of the present disclosure are provided herein in weight per weight ratio (w/w) i.e., the weight in grams of the specific ingredient (e.g., Osmoter, and the polysaccharide of POLLUSTOP®) per 100 gram total weight of the composition.

TABLE 1 studied compositions

| Sample # | Sample name | Solvent |
|---|---|---|
| 1 | POLLUSTOP ® 5% | Water |
| 2 | Osmoter 0.25% | Water |
| 3 | Osmoter 0.5% | Water |
| 4 | Osmoter 0.8% | Water |
| 5 | Osmoter 0.25% + POLLUSTOP ® 5% | Water |
| 6 | Osmoter 0.5% + POLLUSTOP ® 5% | Water |
| 7 | Osmoter 0.8% + POLLUSTOP ® 5% | Water |

Example 2—Laboratory Pollution Models in Skin

Osmoter and POLLUSTOP® were tested alone and in combination for anti-pollution activity using two complementary laboratory models:

Model 1: Ozone exposure, on reconstructed skin equivalents (full thickness tissue).

Model 2: Mixture of pollutants containing heavy metals and atmospheric PM, on reconstructed epidermis.

Both pollution models were based on reconstructed epidermis [manufacture by MatTek corporation, USA, for the ozone exposure model and by CellSystem, Germany, (Troisdorf, Batch 100-AF0828-1) for the pollutant mixture model]. The reconstructed epidermis represents a tridimensional artificial system of human epidermis, comprising normal human epidermal keratinocytes, growing as an integrated three-dimensional cell culture model, perfectly mimicking the human skin in vitro. The reconstructed epidermis exhibits normal barrier functions.

Tissue Preparation

Upon arrival, the epidermis tissues were stored at 4° C. until used. Prior to use, the tissues were removed from the agarose-shipping tray and placed into a 6-well plate containing 0.9 ml of hydrocortisone free assay medium (37° C.). The tissues were allowed to incubate for at least 1 hour at 37° C. and 5% $CO_2$. After this initial incubation, the assay medium was replaced with 0.9 ml of fresh medium (37° C.) and the tissues were treated overnight topically with either the test materials, 100 mg/ml Trolox, or left untreated. Four tissue samples were prepared for each treatment.

Epidermal Viability Evaluation

Epidermis tissues were rinsed and treated with 1 mg/ml 3-[4,5-dimethylthiazol-2-yl]-2,5-diphenyl tetrazolium bromide (MTT) solution for 3 h at 37° C. and 5% $CO_2$. The solution was then removed and replaced with isopropanol, with further 2 h incubation at room temperature. After the extraction, samples were transferred to a 96 well plate for absorbance reading. The absorbance was read at the wavelength of 540/570 nm with a colorimeter (Tecan model Sunrise remote) equipped with a microplate reader using 200 µl of isopropanol as the blank.

Tested Inflammatory Biomarkers

Two inflammatory biomarkers were used i.e., interleukin 1α (IL-1 alpha, or IL-1 α) and Prostaglandins (PGEs).

IL-1 Alpha Levels Detection Procedure:

IL-1 alpha is synthesized and stored in keratinocytes and has been identified as a mediators of skin irritation and inflammation. IL-1 alpha levels were detected in culture medium using ELISA assay. This biomarker was tested for both Ozone and pollutant mix exposure models.

IL-1 alpha has been determined in the medium culture of treated and not treated epidermis, using ELISA test (Enzyme-linked immunosorbent assay). 100 µl of the samples were incubate in a plate pre-coated with primary anti-cytokine antibody for 2 hours at room temperature. At the end, the samples were washed with a suitable buffer. Then 100 µl of secondary biotinylated antibody were added with a further 2 hour incubation step at room temperature. The samples were washed with a suitable buffer and incubated for 30 minutes with streptavidin peroxidase (HP) solution. After 5 washing a colorimetric substrate was added to detect the cytokine bound to the plate. Once a sufficient level of color development had occurred, 50 µl of stop solution (2N sulfuric acid) was added to each well and the absorbance was read at 460 nm using a plate reader.

PGE2 Levels Detection Procedure:

PGEs are synthesized in a variety of cells from arachidonic acid. Arachiconic acid can be released from membrane phospholipids via phospholipase A2, and is then committed to form prostaglandins via the action of cyclooxygenase. Prostaglandin $E_2$ (PGE2) has been shown to be involved in the inflammatory pathway of the skin and is commonly used as a marker to show the efficacy of anti-inflammatory materials. PGE2 levels were detected in culture medium using ELISA assay. This biomarker was tested only for Ozone exposure model.

PGE2 has been determined in the medium culture of treated and not treated epidermis, using ELISA test (Enzyme-linked immunosorbent assay). Series of PGE2 standards was prepared ranging from 7.8 pg/ml to 1000 pg/ml. An ELISA plate was prepared by removing any unneeded strips from the plate frame, remembering to designate two wells each for: total activity (TA) wells, non-specific binding (NSB) wells, maximum binding (MB) wells, and substrate blank wells (B0). 150 µl of tissue culture medium was added to the NSB wells while 100 µl of medium was added to the B0 wells. 100 µl of standard or sample was then added to respective wells. To each of the wells used (except the TA and B0) 50 µl of the PGE2 Alkaline Phosphatase Conjugate was added. Next, 50 µl of PGE2 Alkaline Phosphatase Antibody solution was added to each well (except the TA, NSB and SD wells). The plates were covered and incubated at 2-8° C. for 18-24 hours. After the incubation each well was washed three times with 400 µl of wash buffer. After the last wash, 5 µl of PGE2 Alkaline Phosphatase Conjugate was added to the TA wells and 200 µl of fresh Ellman's Reagent was added to each well. The plate was incubated at room temperature with periodic checks of the absorbance readings at 405 nm using a plate reader.

2.1 Ozone Exposure Model

The ability of the Osmoter and the POLLUSTOP®, alone and in combination, to inhibit the release of the inflammatory mediators IL-1 alpha and PGE2 after exposure to ozone was evaluated.

The tissues were treated overnight topically with the studied compositions detailed in Table 1 above. An inflammatory response in the tissues was then initiated via ozone exposure. Tissues were placed in an exposure chamber which was filled with ozone (20 ppm) for one hour. One set of tissues was not exposed to ozone and served as a non-Ozone exposed control.

The anti-oxidant Trolox (6-hydroxy-2,5,7,8-tetramethyl-chroman-2-carboxylic acid), which is a water-soluble analog of vitamin E and thus, is known in its inflammatory reducing activity was served as a positive control (PC). 100 µg/ml solution of Trolox was applied on the skin samples.

After the ozone exposure the tested compositions were re-applied to the tissues and the tissues were incubated overnight in fresh media. After the 24-hour incubation the cell culture medium was collected and stored at −75° C. until analyzed for cytokines while changes in tissue viability were determined using an MTT assay.

Results:

Epidermal Viability

The epidermal viability observed following exposure to ozone is illustrated in FIG. 1. Viability is expressed as a percent of the Non-Ozone exposed (non-inflamed) controls, which are used to represent 100% viability (skin sample not exposed to ozone represented 100% viability). Skin sample not treated with any of the compositions represented negative control (NC). Trolox which represented positive control showed high viability. The symbol * in FIG. 1 represents $p<0.05$ vs. untreated sample. The results in the figure are expressed as MEAN standard deviation. The cell viability results illustrated that the tested compositions of the present disclosure did not possess any toxicity effect (only a mild decrease of 17% in tissue viability was observed).

IL-1 Alpha Levels

Figure 2:
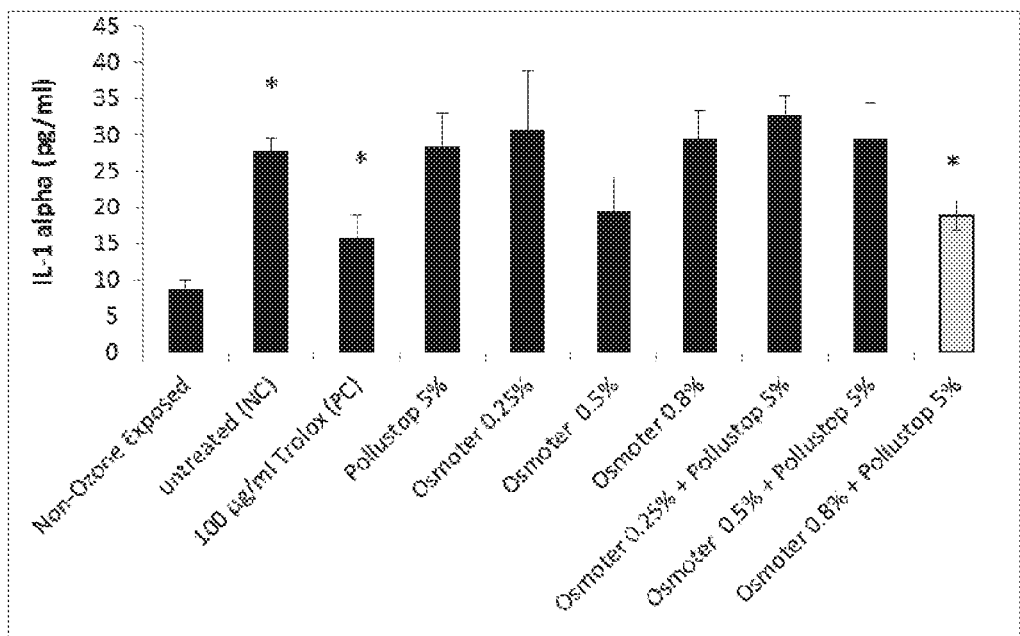
FIG. 2 demonstrates the levels of the cell inflammation mediator IL-1 alpha following exposure to ozone, as observed with samples treated with compositions of Dead Sea extract (at various concentrations), POLLUSTOP® and combination of Dead Sea extract and POLLUSTOP®, according to some embodiments of the invention.

FIG. 2 illustrates the IL-1 alpha levels observed following exposure of the skin equivalents to ozone. Exposure of the epidermis equivalents to ozone resulted in a significant increase in the release of IL-1 alpha (320%). The symbol * in FIG. 2 represents $p<0.05$ vs. untreated sample. The results in the figure are expressed as MEAN f standard deviation. The sample which was not exposed to ozone provided low levels of IL-1 alpha. Similarly, the sample treated with Trolox and serves as positive control provided relatively low levels of IL-1 alpha. While POLLUSTOP® and Osmoter alone illustrated relatively high levels of IL-1 alpha, comparable to those observed with untreated sample (NC), thus indicating an inflammation reaction, a composition with 0.8% (w/w) Osmoter and 5% (w/w) POLLUSTOP® (sample #7 in Table 1) surprisingly illustrated low levels of IL-1 alpha compared to the untreated (NC) sample. Specifically, sample #7 inhibited IL-1 alpha secretion by 32%.

PGE2 Levels

Figure 3:
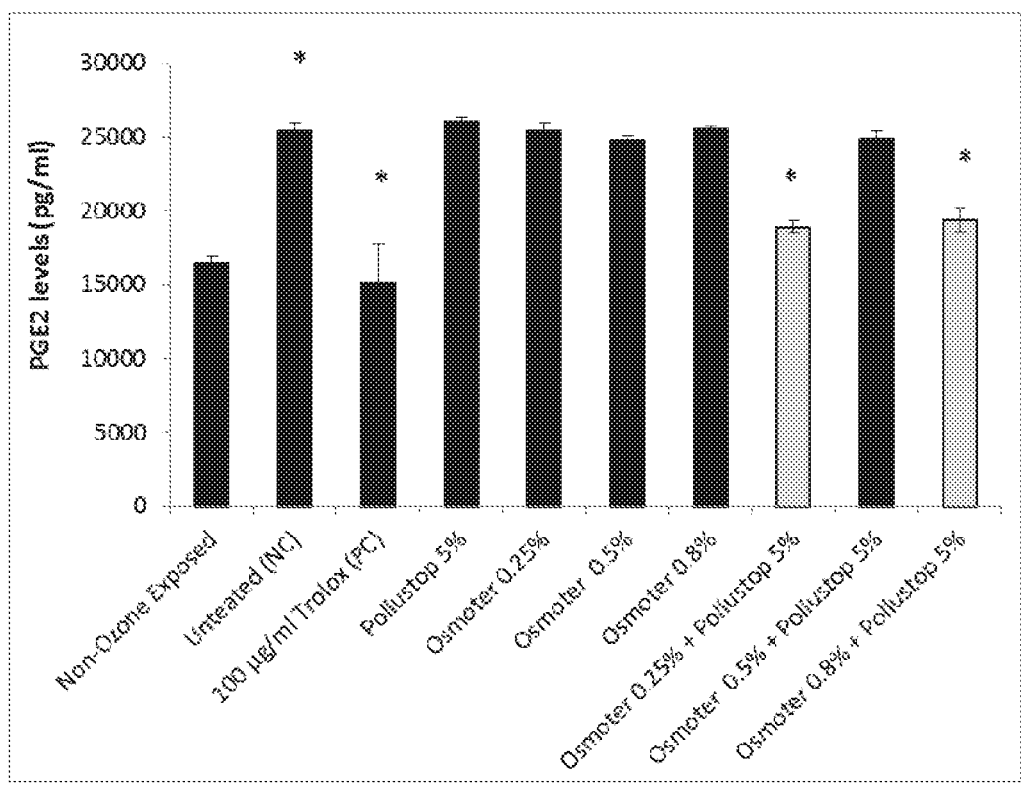
FIG. 3 demonstrates the prostaglandin PGE2 levels following exposure to ozone, as observed with samples treated with compositions of Dead Sea extract (at various concentrations), POLLUSTOP® and combination of Dead Sea extract and POLLUSTOP®, according to some embodiments of the invention.

FIG. 3 illustrates the PGE2 levels observed following exposure of the skin equivalents to ozone. Exposure of the epidermis equivalents to ozone resulted in a significant increase in the release of PGE2 (55%). The symbol * in FIG. 3 represents $p<0.05$ vs. untreated sample. The results in the figure are expressed as MEAN f standard deviation. The sample which was not exposed to ozone provided low levels of PGE2. Similarly, the sample treated with Trolox and serves as positive control provided relatively low levels of PGE2. While POLLUSTOP® and Osmoter alone illustrated relatively high levels of PGE2, comparable to those observed with untreated sample (NC) (thus indicating an inflammation reaction) the composition with 0.25% (w/w) Osmoter and 5% (w/w) POLLUSTOP® (sample #5 in Table 1) and the composition with 0.8% (w/w) Osmoter and 5%

(w/w) POLLUSTOP® (sample #7 in Table 1) surprisingly illustrated low levels of PGE2 compared to the untreated (NC) sample. Specifically, sample #5 inhibited PGE2 secretion by 26% and sample #7 inhibited PGE2 secretion by 24%.

The above results clearly illustrated that while both the Osmoter and the POLLUSTOP® composition as standalone compositions did not show any efficacy in inflammation inhibition, their combination led to a significant inflammation inhibition, illustrating a protection effect against ozone pollution.

2.2 Air Pollutant Mix (Heavy Metals and Standard Atmospheric PM) Exposure Model

The protective effect of Osmoter and POLLUSTOP®, alone and in combination, against air pollutants via inhibition of the release of cell inflammation mediator IL-1 alpha was evaluated.

The heavy metals mixture which was used is detailed in Table 2 below.

TABLE 2

Heavy metals mixture composition

| Element | Mass fraction (ppm) |
|---|---|
| As | 115.5 ± 3.9 |
| Cd | 73.7 ± 2.3 |
| Co | 17.93 ± 0.68 |
| Cr | 402 ± 13 |
| Ni | 81.1 ± 6.8 |
| Pb | 0.655 ± 0.033 |
| Sr | 215 ± 17 |
| Sb | 45.4 ± 1.4 |

Atmospheric PM were obtained as a standard composition consisting of 23 polyhalogenated aromatic compounds (PHAs), 13 polychlorinated biphenyls (PCBs) and 4 chlorinated pesticides. The standard atmospheric PM were provided by National Institute of Standards & Technology (NIST)/EXAXO, STANDARD REFERENCE MATERIAL® 1649b Urban Dust, (See, -s.nist.gov/srmors/certificates/1649B.pdf).

30 µl of the tested compositions were applied on the epidermis with a mixture of pollutants containing heavy metals and atmospheric PM (referred to herein as MIX) and maintained for 48 hours on the epidermis. Every day the epidermis units were washed with PBS buffer and the tested compositions (as well as the control compositions) were applied to the epidermis again. Epidermis units treated only with the air pollutant mix were used as an irritating control. PBS exposure/wash was carried out at 37° C., 5% $CO_2$. At the end of the exposure period (48 h), medium culture was collected for IL-1 alpha determination using ELISA assay.

Results:

Epidermal Viability

MTT assay was performed to evaluate the cell survival.

Figure 4:
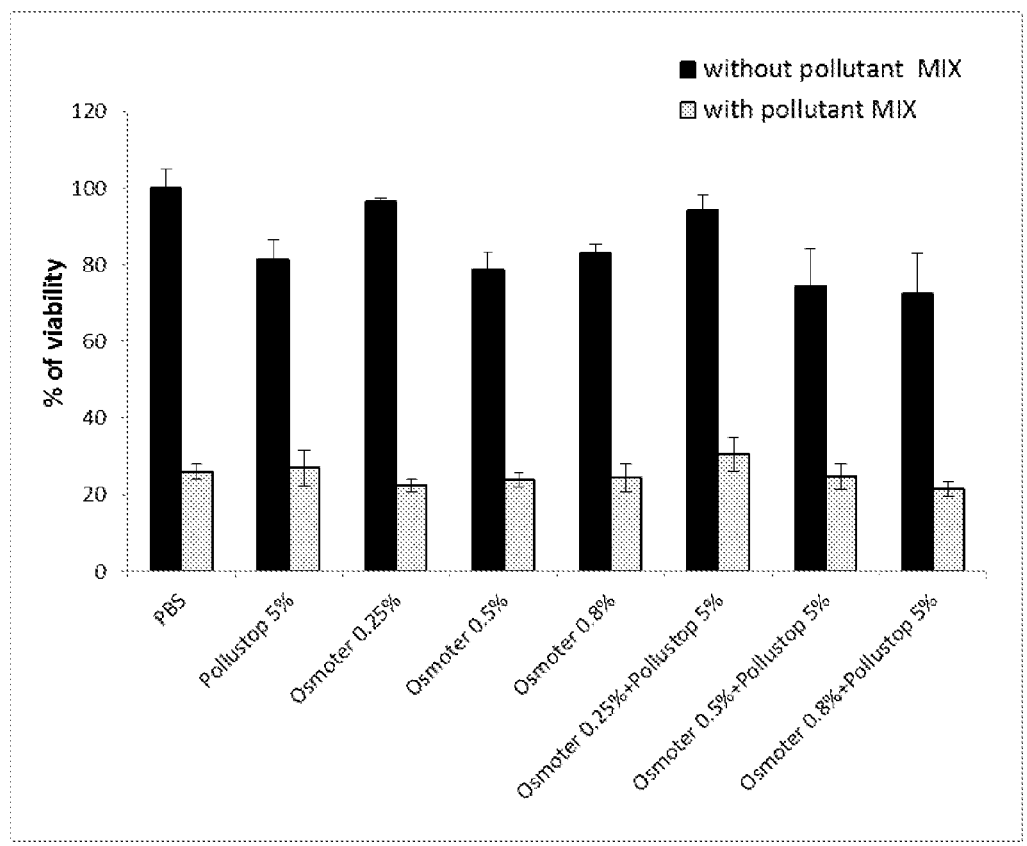
FIG. 4 demonstrates epidermal viability of various samples treated with compositions of Dead Sea extract (at various concentrations), POLLUSTOP® and combination of Dead Sea extract and POLLUSTOP®, without or following exposure of the epidermal to air pollutant mixture, according to some embodiments of the invention.

The epidermal viability observed without and following exposure to air pollutant mix is illustrated in FIG. 4. The results in the figure are expressed as MEAN±standard deviation. All skin samples, control as well as samples treated with the compositions of the present disclosure, not exposed to the pollutant mix illustrated high viability, indicating that the tested compositions of the present disclosure did not possess any toxicity effect to the skin. The skin samples exposed to the air pollutant mix (MIX) show significant sharp decrease in tissue viability by 74% reduction.

IL-1 Alpha Levels

Figure 5:
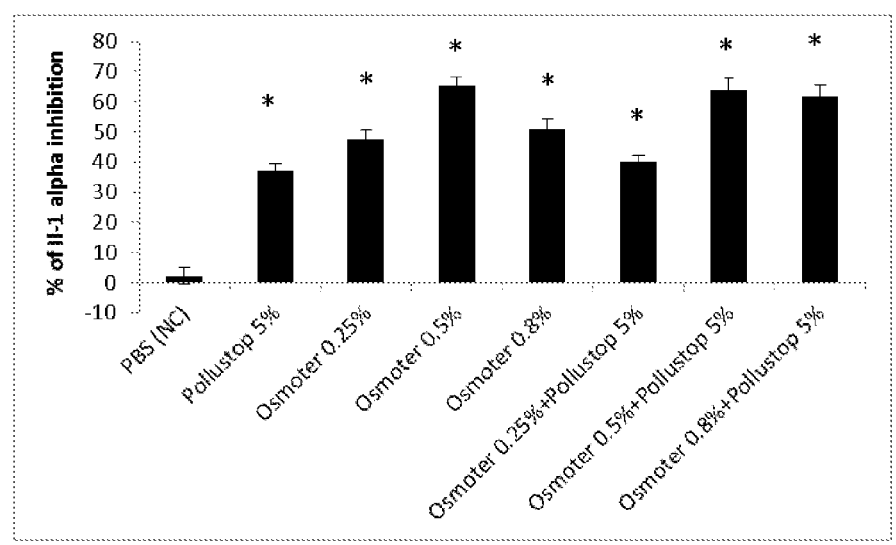
FIG. 5 demonstrates the cell inflammation mediator IL-1 alpha as observed with samples treated with compositions of Dead Sea extract (at various concentrations), POLLUSTOP® and combination of Dead Sea extract and POLLUSTOP®, without or following exposure to air pollutant mixture, according to some embodiments of the invention.

Table 3 details the IL-1 alpha results observed with the model of the air pollutant mix. The results are also illustrated in FIG. 5.

TABLE 3

IL-1 alpha secretion in the air pollutant mix model

| Sample | IL-1 alpha (pg/ml) | SD | % inhibition* |
|---|---|---|---|
| N°1-POLLUSTOP ® 5% | 8.58 | 0.95 | |
| N°1-POLLUSTOP ® 5% + MIX | 39.98 | 11.14 | 36.93 |
| N°2-Osmoter (Dead sea water) 0.25% | 2.39 | 2.21 | |
| N°2-Osmoter (Dead sea water) 0.25% + MIX | 33.27 | 8.32 | 47.52 |
| N°3-Osmoter 0.5% | 11.16 | 3.66 | |
| N°3-Osmoter 0.5% + MIX | 21.96 | 10.47 | 65.36 |
| N°4-Osmoter 0.8% | 8.62 | 1.99 | |
| N°4-Osmoter 0.8% + MIX | 31.17 | 4.05 | 50.83 |
| N°5-Osmoter 0.25% + POLLUSTOP ® 5% | 16.35 | 9.84 | |
| N°5-Osmoter 0.25% + POLLUSTOP ® 5% + MIX | 38.03 | 12.30 | 40.02 |
| N°6-Osmoter 0.5% + POLLUSTOP ® 5% | 20.82 | 13.83 | |
| N°6-Osmoter 0.5% + POLLUSTOP ® 5% + MIX | 22.99 | 6.10 | 63.73 |
| N°7-Osmoter 0.8% + POLLUSTOP ® 5% | 11.03 | 6.70 | |
| N°7-Osmoter 0.8% + POLLUSTOP ® 5% + MIX | 24.26 | 8.62 | 61.74 |

*% IL-1 α inhibition was calculated as follows: 100-(pg/ml IL-1 α release by sample with test compositions/pg/ml IL-1α negative control)*100.

FIG. 5 illustrates the inhibition extent of the secretion of IL-1 alpha observed following exposure of the skin equivalents to air pollutant mix (MIX). The symbol * in FIG. 5 represents $p<0.05$ vs. PBS (negative control, NC). The results in the figure are expressed as MEAN±standard deviation.

It is clear from Table 3 and from FIG. 5 that POLLUSTOP® alone inhibits IL-1 alpha secretion by 36.93%. It is further clear that Osmoter solutions in different concentrations inhibit IL-1 alpha secretion at a range of 47-65%. Further, the compositions with both POLLUSTOP® and Osmoter (at different concentrations) inhibit IL-1 alpha secretion at a range of 40-63%. The latter range is within the range observed with the standalone compositions i.e., combinations of both POLLUSTOP® and Osmoter did not show any added efficacy against exposure to PM and heavy metals.

The results detailed herein above clearly show that Osmoter solutions and POLLUSTOP® solutions contribute to selectivity in protection against urban pollution-induced inflammation.

POLLUSTOP® is a formulation with a specific polysaccharide which has already been proven to provide a mechanical protection against primary pollution using PM-induced oxidative stress in reconstructed epidermis. Also, clinically it was shown that it provides protection against carbon particles and heavy metals [16].

The present study provides support to the alleged protection properties of POLLUSTOP® against exposure to PM and heavy metals. The protections properties are reflected from the inflammation inhibition properties observed using IL-1 alpha as an irritation indicator. The present study also illustrated the protection properties of the Osmoter solutions against exposure to PM and heavy metals. Without wishing to be bound by theory, the Osmoter protection effect may be due to biochemical signaling by the Dead Sea minerals.

It is noted that while both POLLUSTOP® and Osmoter compositions illustrated a significant protection effect against pollution in the above mentioned Model 2 (mixture of pollutants containing heavy metals and atmospheric PM), no protection effect of these individual components was observed against pollution in the above mentioned Model 1 (ozone exposure). Protection against ozone exposure was only observed with compositions comprising both POLLUSTOP® and Osmoter.

Example 3—Testing the Selectivity of the Compositions Against Specific Pollutants As noted herein above, the level of pollution and pollutant concentration may vary throughout the time of the day, by season, geographic location and according to the level of human activity. The necessity of protection of the skin against pollutants may vary accordingly.

For example, while protection against specific pollutant or specific group of pollutants may be necessary at specific geographic location, a different protection might be necessary at another geographic location. The same applies to different seasons and different times of the day.

Thus, while at times broad protection against a variety of pollutants might be necessary, at times protection might be needed only against specific one or more pollutants.

For the purpose of screening specific compositions comprising the active ingredients of the present invention (i.e., DSW and polysaccharide) which possess selective protection properties against pollution, compositions with various concentrations of Osmoter and POLLUSTOP® at various ratios (e.g., weight and/or molecular) are tested for their selective activity against various pollutants (e.g., as detailed herein above, for example urban dust, heavy metals, PM, smoke etc.).

Epidermis tissues are exposed to various pollutants with or without pre-treatment with the compositions with the combinations of Osmoter and POLLUSTOP®.

Viability of the epidermis tissues is tested.

Inflammations tests are performed for example either by IL-1 α and/or PGEs assays as herein described.

At specific concentrations and ratios the compositions illustrate a selective activity against one or more pollutants, at times against two or more pollutants.

This provides the compositions with the selective activity the benefit of utilizing same against specific one or more pollutants, for example with subjects which are exposed to these specific pollutants for example due to geographic location thereof etc.

The invention claimed is:

1. A method for protecting the skin of a subject against at least a secondary one pollutant, the method comprising applying to the skin of said subject a composition comprising as an active combination (i) Dead Sea water; and (ii) biosaccharide-4 wherein said Dead Sea water is a solution having the following composition with salt normality (N) of ±10% of the indicated values:

| | Salt normality (N) | | Salt normality (N) |
|---|---|---|---|
| Na | 0.118 (2.720 g/l) | Rb | $3.5 \times 10^{-6}$ ($<3 \times 10^{-4}$ g/l) |
| K | 0.054 (2.100 g/l) | Sb | $<1.6 \times 10^{-7}$ ($<2 \times 10^{-5}$ g/l) |
| Ca | 0.873 (35.000 g/l) | Sr | $7.6 \times 10^{-3}$ (0.670 g/l) |
| Mg | 3.815 (92.700 g/l) | V | $<7.9 \times 10^{-5}$ ($<0.004$ g/l) |
| Ba | $6.6 \times 10^{-5}$ (0.009 g/l) | Th | $<8.6 \times 10^{-8}$ ($<2 \times 10^{-5}$ g/l) |
| Cd | $<1.8 \times 10^{-7}$ ($<2 \times 10^{-5}$ g/l) | U | $<8.4 \times 10^{-8}$ ($<2 \times 10^{-5}$ g/l) |
| Co | $<3.4 \times 10^{-5}$ ($<0.002$ g/l) | Zn | $<3.06 \times 10^{-5}$ ($<0.002$ g/l) |
| Cu | $<3.15 \times 10^{-5}$ ($<0.004$ g/l) | Cl | 9.75 (346 g/l) |
| Cr | $<3.85 \times 10^{-4}$ ($<0.02$ g/l) | Br | 0.175 (14 g/l) |
| Fe | $<3.58 \times 10^{-5}$ ($<0.002$ g/l) | B | 0.011 (0.120 g/l) |
| Li | $5.76 \times 10^{-3}$ (0.040 g/l) | As | $2.7 \times 10^{-5}$ (0.002 g/l) |
| Mn | $1.82 \times 10^{-4}$ (0.010 g/l) | I | $6.30 \times 10^{-7}$ ($8 \times 10^{-8}$ g/l) |
| Mo | $<1.04 \times 10^{-6}$ ($<10^{-4}$ g/l) | SiO2 | $<3.33 \times 10^{-4}$ ($<0.02$ g/l) |
| Ni | $<3.4 \times 10^{-5}$ ($<0.002$ g/l) | SiO4 | $<2.2 \times 10^{-3}$ ($<0.2$ g/l); |
| Pb | $<9.6 \times 10^{-8}$ ($<2 \times 10^{-5}$) | | | wherein said secondary pollutant is ozone; and wherein said active combination synergistically protects the skin of said subject against ozone.

2. The method according to claim 1, wherein said biosaccharide-4 is present in said composition at a concentration of between about 0.5% (w/w) to about 5% (w/w) of the total weight of the composition.

3. The method according to claim 1, wherein said Dead Sea water is present in said composition at a concentration of between about 0.1% to about 2.5% (w/w) of the total weight of the composition.

4. The method according to claim 1, wherein said biosaccharide-4 is present in said composition at a concentration of about 5% (w/w) and wherein said Dead Sea water is present in said corn position at a concentration of between about 0.25% to about 0.8% (w/w) of the total weight of the composition.

5. The method according to claim 1, wherein said composition is comprised within a patch and/or being in a form selected from a film, a serum, a lotion, an ointment, a gel, a cream, a water in oil or oil in water emulsion, a shampoo, a moisturizer, a sunscreen, a cream, a stick, a spray, an aerosol, foam, a paste, a mousse, a solid, semi-solid, or a liquid make-up, a foundation, and a make-up.

6. The method according to claim 1, wherein said composition is formulated as a pharmaceutical or a cosmetic formulation, optionally further comprising at least one drug molecule.

* * * * *

UNITED STATES PATENT AND TRADEMARK OFFICE
CERTIFICATE OF CORRECTION

| | | |
|---|---|---|
| PATENT NO. | : 12,016,947 B2 | Page 1 of 1 |
| APPLICATION NO. | : 17/399709 | |
| DATED | : June 25, 2024 | |
| INVENTOR(S) | : Portugal Cohen et al. | |

It is certified that error appears in the above-identified patent and that said Letters Patent is hereby corrected as shown below:

In the Claims

Column 27, Claim 1, Line 54, please delete "at least"

Column 27, Claim 1, Line 55, please delete "secondary one pollutant," and replace with -- secondary pollutant, --

Column 28, Claim 1, Line 3, please delete "biosaccharide-1" and replace with -- Biosaccharide gum-4; --

Column 28, Claim 2, Lines 28-29, please delete "biosaccharide-1" and replace with -- Biosaccharide gum-4 --

Column 28, Claim 4, Lines 37-38, please delete "biosaccharide-1" and replace with -- Biosaccharide gum-4 --

Column 28, Claim 4, Line 40, please delete "corn position" and replace with -- composition --

Signed and Sealed this
Thirtieth Day of July, 2024

Katherine Kelly Vidal
*Director of the United States Patent and Trademark Office*